United States Patent [19]

Chubachi et al.

[11] Patent Number: 4,566,333

[45] Date of Patent: Jan. 28, 1986

[54] FOCUSING ULTRASONIC TRANSDUCER ELEMENT

[75] Inventors: Noriyoshi Chubachi, 4-6-203, Katahira 1-chome, Sendai-shi, Miyagi-shi; Junichi Kushibiki, 48, Aza Nakazaike, Arai, Sendai-shi, Miyagi-ken; Kouichi Nakanishi, Aichi, all of Japan

[73] Assignees: Keisuke Honda; Noriyoshi Chubachi; Junichi Kushibiki, all of Aichi, Japan

[21] Appl. No.: 632,206

[22] Filed: Jul. 18, 1984

[30] Foreign Application Priority Data

Aug. 8, 1983 [JP] Japan .................................. 58-144728

[51] Int. Cl.⁴ .......................................... G01N 29/00
[52] U.S. Cl. ..................................... 73/642; 73/606; 73/629; 73/644

[58] Field of Search ................. 73/606, 607, 642, 644, 73/629

[56] References Cited

U.S. PATENT DOCUMENTS 4,420,979 12/1983 Momii et al. ........................ 73/606
4,459,852 7/1984 Chubachi et al. .................... 73/642

FOREIGN PATENT DOCUMENTS

57-80556 5/1982 Japan .................................... 73/606

*Primary Examiner*—Howard A. Birmiel
*Attorney, Agent, or Firm*—Burgess, Ryan & Wayne

[57] ABSTRACT

A focusing ultrasonic transducer element comprising an ultrasonic propagating medium and an ultrasonic transmitting and receiving transducer. The ultrasonic propagating medium is provided with a convex spherical or cylindrical portion in one end and a concave spherical or cylindrical portion in the other end.

8 Claims, 15 Drawing Figures

PRIOR ART

FIG. 1

PRIOR ART

FIG. 2

PRIOR ART

PRIOR ART

FOCUSING ULTRASONIC TRANSDUCER ELEMENT

BACKGROUND OF THE INVENTION

The present invention relates to a focusing ultrasonic transducer element for producing a focusing ultrasonic beam used in an ultrasonic microscope.

In recent years, a mechanical scanning type ultrasonic microscope has been developed in which a microscopic or macroscopic structure and acoustic properties of a substance are observed and measured by using a focusing ultrasonic beam. In the principle of the ultrasonic microscope of this type, a conically focused ultrasonic beam is irradiated on specimen and the focus position of the ultrasonic beam is laterally or vertically shifted on the surface of the specimen, and then the reflected or passed waves of the ultrasonic beam produced by differences between elastic properties of respective points in the specimen are detected and converted to electric signals by an ultrasonic transducer. The image of the ultrasonic microscope is obtained by two-dimensionally displaying the electric signals on a cathode ray tube or by recording these signals in an X-Y recorder. A transducer for forming a focusing ultrasonic beam is typically of a lens system or a system in which an ultrasonic transducer is formed on a convex or concave spherical surface and so on. Also, the ultrasonic microscope is classified into a passing type and a reflection type by the arrangement of the ultrasonic transducer.

In such ultrasonic microscope, as typical means for forming a focusing ultrasonic beam, an acoustic lens system (see Japanese Patent Application No. 18446/1974) or a system in which an ultrasonic trnsducer is constructed on a convex or concave spherical surface (see Japanese Patent Application Nos. 999953/1976, 127498/1976 and 155766/1980) and so on have been practicably used. In the acoustic lens system, a plane sound wave produced in the ultrasonic transducer propagates through an acoustic lens medium, is focused by its acoustic lens portion and is irradiated through an acoustic medium to a specimen. A focal length (F) in this lens system is approximately represented by the following fomula:

$$F = R/(1-C)$$

where R is the radius of curvature of the sphere in the lens system and $C = V\Omega/Vl$, where $V\Omega$ is the velocity of sound in the acoustic medium and Vl is the velocity of sound of the longitudinal wave in the lens material. A resolving power is approximately proportional to $\lambda \cdot F/D$, where $\lambda$ is the wave length of the sound wave in the acoustic medium and D is the diameter of the lens aperture. When a material having high velocity of sound is selected as an acoustic lens medium, the focal length of the ultrasonic beam becomes short, the ultrasonic beam is made narrow in the focal point and the high resolving power of the ultrasonic microscope is expected, but, because the value of its velocity of sound is finite a spherical aberration is produced in the lens system. Usually, Z-cut sapphire $\{V\Omega = 1483 m/s (20° C.)\}$ in which the attenuation in the propagation of the ultrasonic beam is very small and its velocity of sound is high is practically used as a lens material. When the sapphire and water $\{V\Omega = 1483 m/s (20° C.)\}$ as an acoustic medium are used, C becomes about 0.133, F does not almost correspond with R and a beam waist W of the focusing ultrasonic beam becomes larger than that of the focusing ultrasonic beam which is obtained in the ideal state of F=R and the resolving power is lowered.

There is a fused quartz ($SiO_2$) as a cheap lens material in which the attenuation in propagation of a high frequency ultrasonic wave is relatively small. However, the velocity (Vl) of sound of the fused quarts ($SiO_2$) is 5973m/s, the focal length (F) becomes larger than the radius (R) by 33% and the resolving power becomes lower.

As stated above, because the material having a low velocity of sound makes the focal length F long and makes the resolving power low, the propagating length in an accoustic medium becomes long and signals detected by an ultrasonic transducer become small due to the attenuation in propagation of an ultrasonic wave. The use of the material such as fused quartz is limited for the lens material having a high resolving power.

On the other hand, in the focusing ultrasonic transducer element in which an ultrasonic transducer is arranged on a convex or concave spherical surface, the ultrasonic wave produced by the ultrasonic transducer is ideally converged to one point. In other words, because the focusing ultrasonic transducer element is constructed such as a concentric sphere and the ultrasonic wave is perpendicularly incident upon a boundary surface of the acoustic medium, there is feature that the ultrasonic wave is converged to the center of the concentric sphere without aberration.

However, it is technically not always easy to uniformly form on the concentric sphere an ultrasonic transducer which is efficiently driven.

Also, in the focusing ultrasonic transducer element in which the ultrasonic transducer is supported by a substrate, because the substrate for supporting the ultrasonic transducer is thin and is operated in a composite resonating mode, a frequency band which can be efficiently used is narrow and a response to pulses is low. Furthermore, in a transducer for superhigh frequency, because the size of this transducer and the radius of a spherical surface for mounting it become very small and a thinner substrate becomes necessary for the transducer, the strength of the substrate becomes weak and the transducer cannot be adapted for the high frequency.

In a focusing ultrasonic transducer element having a very thick substrate, the ultrasonic waves can not be efficiently generated and detected, because the area of an ultrasonic transducer becomes too large and the electrostatic capacity of a transducer become large for generating a focusing ultrasonic beam having a wide aperture angle.

SUMMARY OF THE INVENTION

The object of the present invention, therefore, provides a focusing ultrasonic transducer element for a high resolving power in which a narrowly focused ultrasonic beam is formed.

The another object of the present invention provides a focusing ultrasonic transducer element having a wide dynamic range and an improved S/N ratio in the image and quantitative measurements with the ultrasonic microscope.

The additional another object of the present invention provides a focusing ultrasonic transducer element in which an inexpensive fused quartz having a low velocity of sound can be used as well as a material having a high velocity of sound such as sapphire.

These and other objects described herein are achieved by a focusing ultrasonic transducer element comprising an ultrasonic propagating medium having a convex spherical portion formed with one portion of a sphere in one end thereof and a concave spherical portion formed with one portion of a sphere in the other end thereof and an ultrasonic transmitting and receiving transducer attached on the surface of said convex spherical portion, an axis of symmetry of the convex spherical portion being aligned with that of the concave spherical portion and a center of the convex spherical portion being offset from that of the concave spherical portion, and an ultrasonic transducer mounted on the surface of the convex spherical portion.

BRIEF DESCRIPTION OF THE DRAWINGS

FIGS. 4 (a) to (d) are diagrams for explaining the formations of focusing ultrasonic beams with an ultrasonic transducer mounted on concave or convex spherical portions.

DESCRIPTION OF THE PREFFERED EMBODIMENTS

Before the embodiments of the present invention are explained, the principle of an ultrasonic microscope and the prior art are explained.

Figure 1:
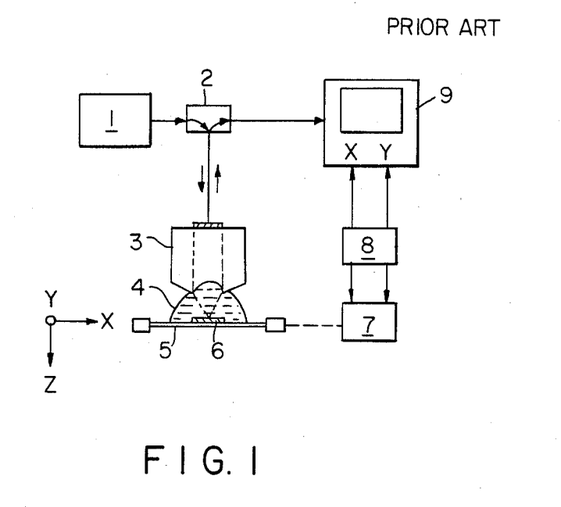
FIG. 1 is a block diagram for explaining the principle of a reflecting type ultrasonic microscope according to the prior art.

FIG. 1 shows a block diagram of a reflection type ultrasonic microscope for an image measurement, in which an acoustic lens is used for producing a focusing ultrasonic beam. In FIG. 1, an electric signal from a high frequency pulse oscillator 1 is supplied through a directional coupler 2 to a focusing ultrasonic transducer 3 and is converted to an ultrasonic beam with the focusing ultrasonic transducer 3. The ultrasonic beam is irradiated on a specimen 6 through an acoustic medium 4, the speciment 6 being fixed on a specimen supporting plate 5 and being arranged in a near portion of the focal point. The specimen supporting plate 5 is driven in X and Y directions by a scanning unit 7. However, the focusing ultrasonic transducer 3 may be driven in the X and Y directions instead of the specimen supporting plate 5. Also, the scanning unit 7 is controlled by a scanning control circuit 8. The reflection wave reflected by the specimen 6 is supplied again to the focusing ultrasonic transducer 3, is converted to the electric signal and is supplied to a display unit 9 through the directional coupler 2. An image of the ultrasonic microscope is displayed at the display unit 9.

Such measurement in which the acoustic property of the specimen is read out of the image of the ultrasonic microscope as a function of position is called an image measurement with the ultrasonic microscope.

In this image measurement, the ultrasonic microscope not only displays an ultrasonic image by arranging the specimen 6 on the focal plane of the ultrasonic beam in the acoustic medium (water is used in general), but also the ultrasonic microscope is mostly used by positively offsetting the specimen 6 from the focal plane. This is the feature of the ultrasonic microscope and the change in the specimen which cannot be viewed by the conventional optical microscope and the electron microscope may be viewed with a fine contrast.

Figure 2:
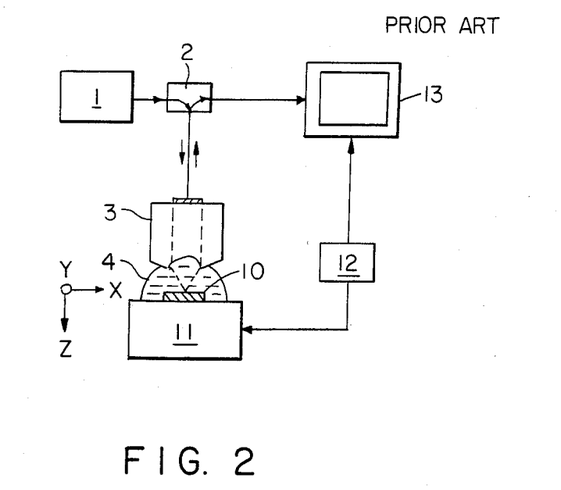
FIG. 2 is a block diagram for explaining the principle of the measurement of acoustic properties with a reflecting ultrasonic microscope according to the prior art.

FIG. 2 is a block diagram of an ultrasonic microscope according to the prior art for quantitative measurement. The same reference numerals as used in FIG. 1 denote the same parts in FIG. 2. In the ultrasonic microscope in FIG. 2, the specimen 10 (e.g. solid substance) is vertically moved to a Z-axis direction by a driving unit 11 which is controlled by a control unit 12 to approach the ultrasonic transducer 3. The output of the ultrasonic transducer 3 is viewed by the recorder 13. The curve of the output of the ultrasonic transducer 3 is a V(Z) curve or acoustic property curve, whose formation depends on the acoustic property of a substance.

Figure 3:
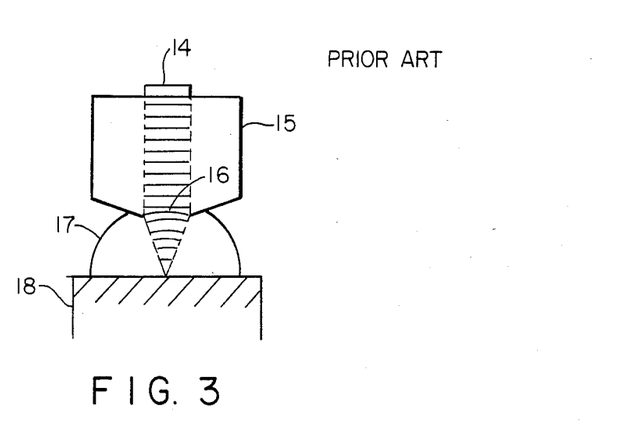
FIG. 3 is a diagram for explaining the formation of a focusing ultrasonic beam with an acoustic lens system according to the prior art.
Figure 4A:
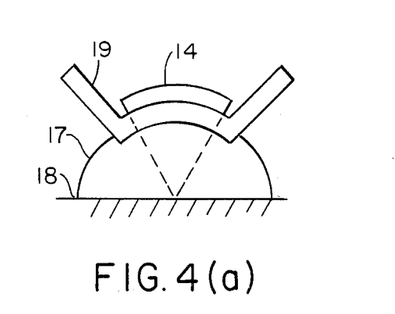
Figure 4B:
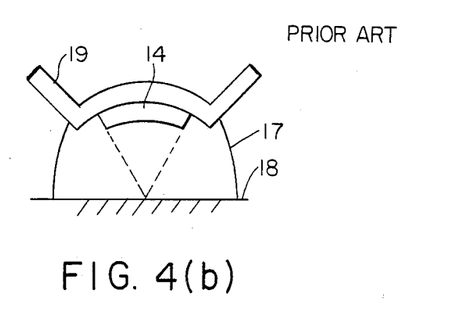
Figure 4C:
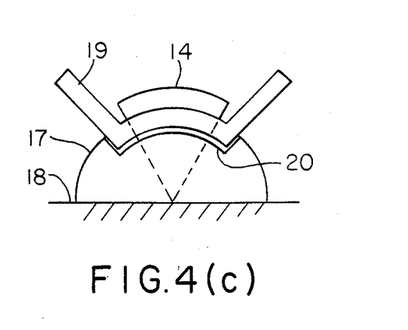
Figure 4D:
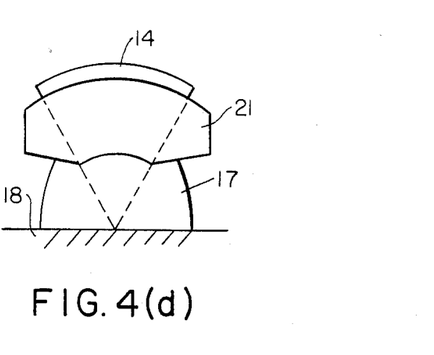

In the ultrasonic microscope constructed as shown above, as a typical means for producing an ultrasonic beam, the acoustic lens system as shown in FIG. 3 (see Japanese Paent Aplication No. 18446/1975), the system in which the ultrasonic transducer is arranged on a concave or convex sphere (see Japanese Patent Application Nos. 99953/1976, 127498/1976 and 155766/1980) and so on have been practicably used.

In the acoustic lens system as shown in FIG. 3, a plane sound wave produced by an ultrasonic transducer 14 is propagated through an acoustic lens medium 15, is focused by an acoustic lens portion 16 and is irradiated on a specimen 18 through an acoustic medium 17. The focal length (F) can be approximately represented by the following fomula:

$$F = R/(1-C)$$

where R is a radius of curvature of a lens, C is $V\Omega/Vl$, and where $V\Omega$ is a velocity of sound of an acoustic medium and Vl is a velocity of sound of the longitudinal wave in a lens material. A resolving power d is approximately proportional to $\lambda \cdot F/D$ where $\lambda$ is a wavelength of a sound wave in acoustic medium 17 and D is a diameter of a lens aperture. In a material having a high velocity of sound for the acoustic lens medium 15, the focal length of the ultrasonic beam becomes short, the ultrasonic beam is narrowly converged in the focal point and the high resolving power is expected. However, because the velocity of sound in the material is finite, a spherical aberration of the lens is produced. Usually, as a material of a lens, a Z-cut sapphire (Vl=11180m/s) having the very small attenuation of propagation of the ultrasonic wave and the high velocity of sound is practically used. When the sapphire and water {VΩ=1483m/s (20° C.)} as an acoustic medium are used, C becomes about 0.133, F does not almost correspond with R, a beam waist W (i.e., the distance between diametrically opposed points at which the beam intensity is half its maximum value) of the focusing ultrasonic beam becomes larger than that of the focusing ultrasonic beam which is obtained in the ideal state of F=R and the resolving power is lowered.

Fused quartz ($SiO_2$) is available as an inexpensive lens material in which the attenuation of propagation of a high frequency ultrasonic wave is comparatively large in comparison with the expensive sapphire. However, the velocity (Vl) of sound of the fused quartz ($SiO_2$) is 5973m/s, and in this case, the focal length (F) becomes larger than the radius (R) by 33% and the resolving power becomes lower.

As stated above, because the propagating length in the acoustic medium becomes long and the signal becomes small due to the attenuation of propagation of the ultrasonic wave, in addition to the material having the low velocity of sound, makes the focal length F long and makes the resolving power low use of the material such as fused quartz is limited for a lens material for obtaining the high resolving power.

On the other hand, in the system as shown in FIGS. 4(a) to 4(d), because the ultrasonic transducer 14 is arranged on the concave or convex spherical surface, the ultrasonic wave produced by the ultrasonic transducer 14 is naturally converged. In other words, because the focusing ultrasonic transducer 14 is constructed on such a portion of a concentric sphere and the ultrasonic wave is perpendicularly incident upon a boundary between two media, there is the feature that the ultrasonic wave is converged to the center of the concentric sphere without aberration. In FIGS. 4(a) to 4(d), the reference numerals 18, 19, 20 and 21 respectively denote a specimen, a substrate, an acoustic matching layer and an ultrasonic propagation medium.

However, it is technically not always easy to uniformly form on the concentric sphere the ultrasonic transducer which is efficiently driven. Also, in the focusing ultrasonic transducer of FIGS. 4(a) to 4(c), because the substrate 19 for supporting the ultrasonic transducer 14 is thin and consequently is operated as a composite resonating mode, a frequency band which can be efficiently used is narrow and a response to a pulse is poor. Furthermore, in an ultrasonic microscope using an ultrasonic transducer of super high frequency, because the size of this transducer and the radius of the spherical surface for mounting it become very small and a thin substrate 19 becomes necessary for supporting the ultrasonic transducer, the strength of this substrate is weak and is not adapted for the ultrasonic microscope. Also, in the instance of FIG. 4(d), because the area of the ultrasonic transducer 14 becomes too large for producing a focusing ultrasonic wave in which an aperture angle is completely wide, the capacitance of the ultrasonic transducer becomes large, so that the ultrasonic wave is not efficiently produced and detected by the ultrasonic transducer.

Figure 5:
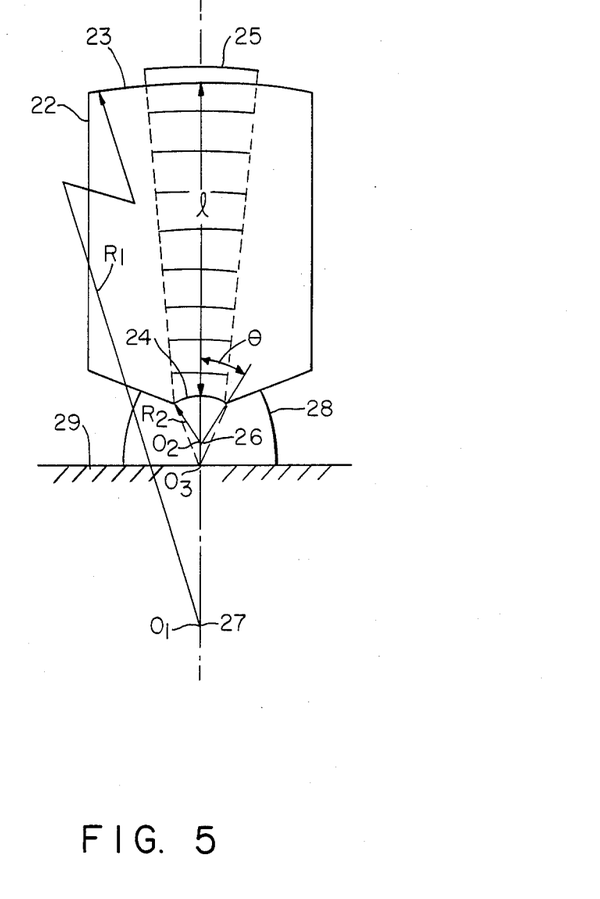
FIG. 5 is a sectional view of a focusing ultrasonic transducer element according to a first embodiment of the present invention.

Preferred embodiments of the present invention will now be described with reference to the accompanying drawings. FIG. 5 is a sectional view of a focusing ultrasonic transducer element according to the present invention. An ultrasonic propagating medium 22 forms a convex spherical portion 23 at one end and a concave spherical lens portion 24 at the other end. An ultrasonic transducer 25 is formed at one portion on the convex spherical portion 23 of the one end of the ultrasonic propagating medium 22. The axis of symmetry of the concave spherical lens portion 24 of the ultrasonic propagating medium 22 is aligned with the axis of symmetry of the convex spherical portion 23 on which the ultrasonic transducer 25 is formed. The center 26 of the concave spherical lens portion 24 is offset from the center 27 of the convex spherical portion 23, and the concave spherical lens portion 24 and the convex spherical portion 23 are formed into such a meniscus lens. Also, the concave spherical lens portion 24 is inserted into the acoustic medium 28 and is opposite to the specimen 29.

In the focusing ultrasonic transducer element constructed as stated above, the ultrasonic wave produced by the ultrasonic transducer 25, which is formed on one portion of the convex spherical portion (radius of curvature $R_1$) having a large radius of curvature, is propagated through the ultrasonic propagating medium to converge into one point $O_1$ of the axis of symmetry. The propagating wave is then converged into the focal point $O_3$ by the lens effect of the concave spherical lens portion 24 (the radius of curvature is $R_2$ and the aperture angle is $\theta$).

As stated above, in the focusing ultrasonic transducer according to the present invention, the defects in each of systems for focusing ultrasonic waves are completely improved by using both of the focusing effect due to the acoustic lens in FIG. 3 and focusing effect due to the ultrasonic transducer constructed on the spherical surface as shown in FIG. 4. As an ultrasonic propagating medium, the material having a comparatively low velocity of sound such as fused quartz ($SiO_2$) is used as well as the material having a high velocity of sound such as sapphire.

TABLE

| l (mm) | $R_2$ (mm) | $R_1$ (mm) | $\theta$ (degree) |
|---|---|---|---|
| 8.5 | 1.26 | 14.6 | 30 |

The above table shows the parameters of the focusing ultrasonic transducer element according to the embodiment of the present invention. In the table, the fused quartz ($SiO_2$) is used as the ultrasonic propagating medium 22, water is used as the acoustic medium 28, and the focusing ultrasonic transducer element is designed to operate in the frequency band of 200Hz.

In this embodiment, the focal length F is represented by F=1.24R=1.56mm, and the focal length becomes shorter than the focal length (F=1.33R) by about 7% in the case in which the fused quartz is used as a acoustic lens system. The resolving power in this embodiment is improved by the prevention of spherical aberration.

Figure 6A:
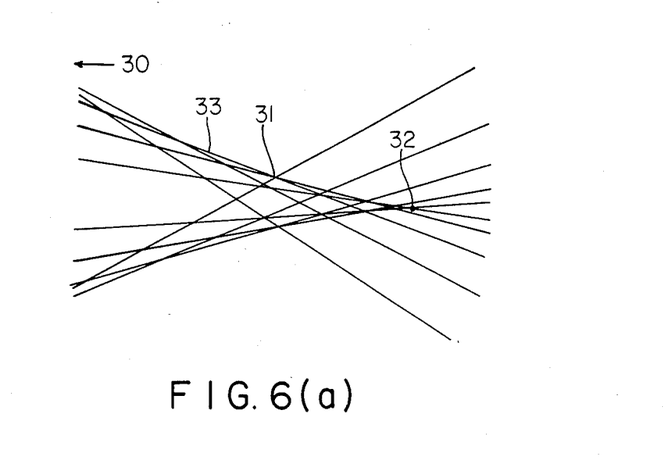
FIG. 6(a) is a view for showing a focusing state of an ultrasonic wave near the focal point according to the acoustic lens system of the prior art.
Figure 6B:
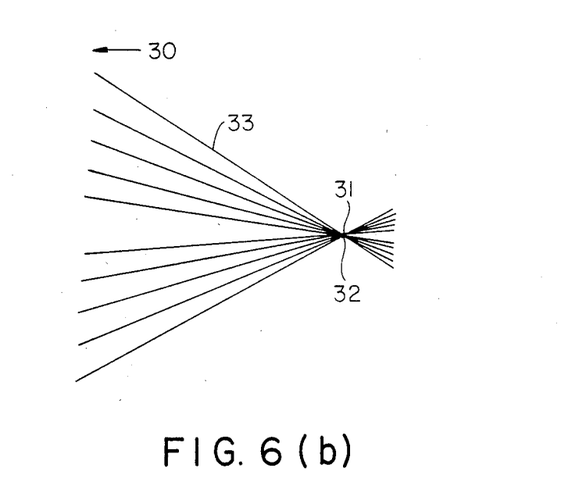
FIG. 6(b) is a view for showing a focusing state of an ultrasonic wave near the focal point according to the present invention.

Now, in order to intuitively explain the improvement of the resolving power due to the improvement of the spherical aberration of the focusing ultrasonic transducer element, FIGS. 6(a) and 6(b) show the states of the focusing ultrasonic wave near the focal point by way of geometric optics. FIG. 6(a) is a view of the case of the acoustic lens system and FIG. 6(b) is a view of the case of the focusing ultrasonic transducer according to the present invention. In FIGS. 6(a) and 6(b), reference numerals 30, 31, 32 and 33 respectively denote an input side of the ultrasonic wave, a focal point, a paraxial focal point and a focusing ultrasonic wave.

According to the effects described above, in the present invention, the beam waist W of the focusing ultrasonic beam 33 in the focal point 31 becomes narrow and the resolving power is improved.

In the above embodiment, the focusing ultrasonic transducer element is used to form the ultrasonic wave focused such as a point, but the same construction is adapted for an focusing ultrasonic transducer (Japanese Patent Application No. 107402/1981) producing an ultrasonic beam focused such as a line.

Figure 7:
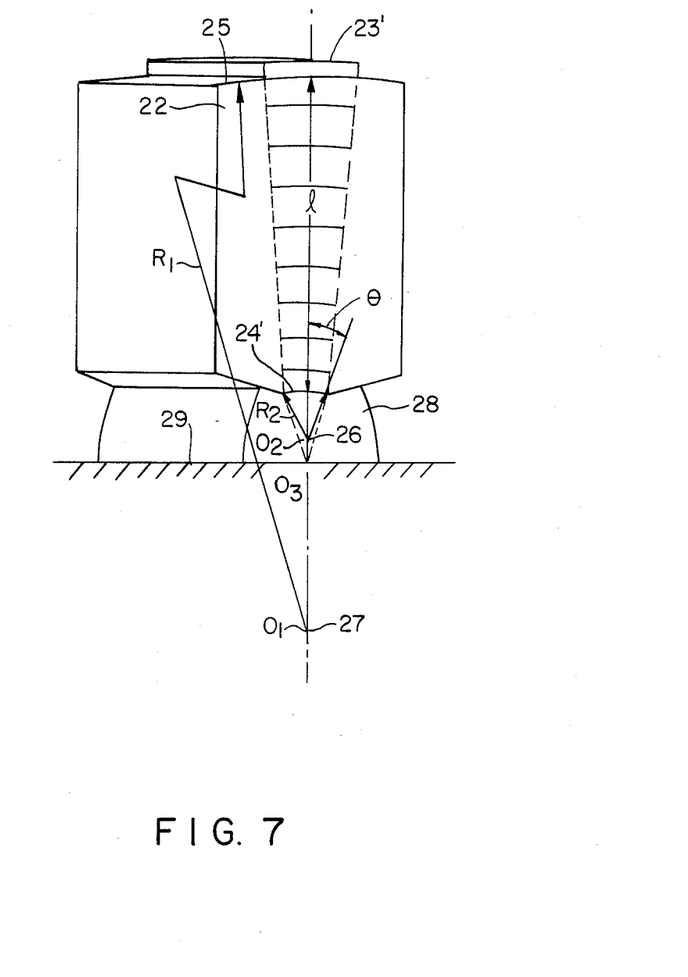
FIG. 7 is a perspective view of a focusing ultrasonic transducer element according to a second embodiment of the present invention.

FIG. 7 is a perspective view of a focusing ultrasonic transducer element according to a second embodiment of the present invention and the same reference numerals as shown in FIG. 5 denote the same parts in FIG. 7. In this embodiment, an ultrasonic propagating medium 22 and an acoustic medium 28 are elongated in the vertical direction to an axis of symmetry and the convex spherical portion 23 and the concave spherical lens portion 24 are respectively replaced with a convex cylindrical surface portion 23' and a concave cylindrical surface portion 24'.

According to the present invention as described above, because the ultrasonic transducer and the spherical lens portion or the cylindrical lens portion are constructed on the eccentric spherical ultrasonic propagating medium, a focusing ultrasonic beam having a high resolving power is produced, the decrease of the attenuation of propagation in the acoustic medium is reached, the dynamic range can be widened and S/N ratio is improved. Furthermore, an inexpensive fused quartz ($SiO_2$) can be used as well as a material having a high velocity of sound such as sapphire for the ultrasonic propagating medium.

Figure 8:
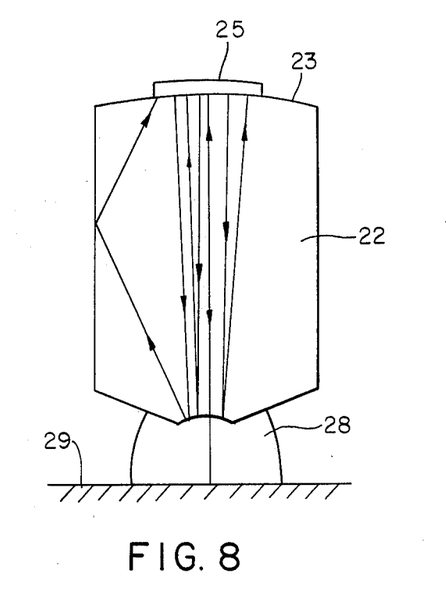
FIG. 8 is a sectional view of an ultrasonic transducer element for explaining defects of the focusing ultrasonic transducer of FIGS. 5 and 7.
Figure 9:
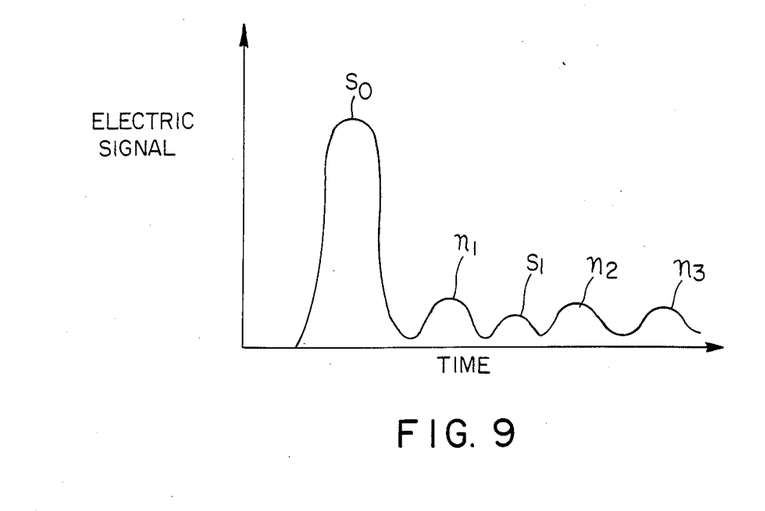
FIG. 9 is a view for showing the strength of energy in the focusing ultrasonic transducer elements of FIGS. 5 and 7 with the lapse of time.

In the focusing ultrasonic transducer elements as shown in FIGS. 5 and 7, one part of the ultrasonic wave produced from the ultrasonic transducer 25 is reflected by the boundary surface of the concave spherical lens portion 24 in the ultrasonic propagating medium 22 due to the discontinuity between the acoustic impedances of the ultrasonic propagating medium 22 and the acoustic medium 28 as shown in FIG. 8, and the reflected ultrasonic wave is converted to a electric signal by the ultrasonic transducer 25. Therefore, as shown in FIG. 9, the reflected ultrasonic energies $n_1$, $n_2$ and $n_3$ in addition to the ultrasonic energy $s_1$ reflected by the specimen 29 are detected by the ultrasonic transducer 25. There are defects that this shows that the ultrasonic energy produced by the ultrasonic transducer 25 is not efficiently irradiated to the specimen and the S/N ratio of the signal from the specimen is lowered.

Figure 10:
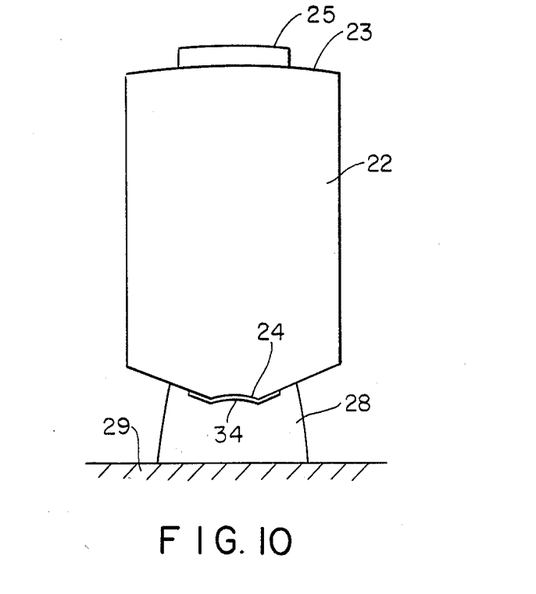
FIG. 10 is a view of a focusing ultrasonic transducer element according to a third embodiment of the present invention.

FIG. 10 shows a sectional view of a focusing ultrasonic transducer element according to a third embodiment of the present invention. In FIG. 10, reference numerals 22, 23, 24, 25, 28 and 29 respectively denote an ultrasonic propagating medium, a convex spherical portion, a concave spherical lens portion, an ultrasonic transducer, acoustic medium and a specimen. Since these constituents are same as the focusing ultrasonic transducer element as shown in FIG. 5, the explanation of these constituents is omitted. However, it is different from the focusing ultrasonic transducer element in FIG. 5 that an acoustic impedance matching layer 34 is attached to the concave spherical lens portion 24 in the present embodiment.

In this focusing ultrasonic transducer element according to the present embodiment, the most suitable impedance $Z_f$ of the acoustic impedance matching layer 34 can be represented by $$Z_f = \sqrt{Z_1 \cdot Z_\Omega}$$

where $Z_1$ is a characteristic acoustic impedance of the ultrasonic propagating medium 22 and $Z\psi$ is a characteristic acoustic impedance of the acoustic medium 28. When the acoustic wave length propagating the material of the acoustic impedance matching layer 34 is denoted by $\lambda$ and the acoustic impedance matching layer 34 having the most suitable acoustic impedance $Z_f$ is attached between the spherical lens portion 24 and acoustic medium 28 to become $\lambda/4$ in thickness, the reflection in the boundary surface of the concave spherical lens portion 24 of the ultrasonic propagating medium 22 can be completely prevented.

When sapphire is used for the ultrasonic propagating medium 22 and water is used for the acoustic medium 28, the material used for the acoustic impedance matching layer 34 is $SiO_2$, Chalcogenide glass, Borosilicate glass and a compound consisting of Boron and Silicon. These materials are adapted for the other combinations of many kinds of materials of the ultrasonic propagating medium 28 and the acoustic medium 22.

Figure 11:
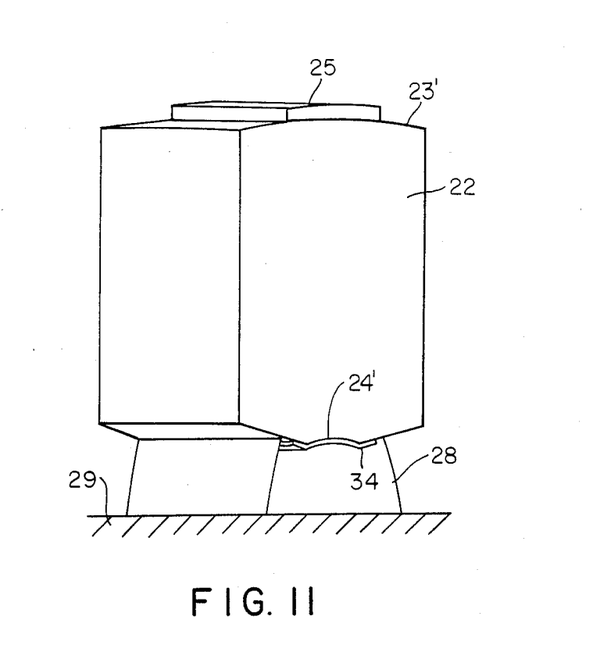
FIG. 11 is a view of a focusing ultrasonic transducer element according to a fourth embodiment of the present invention.

FIG. 11 shows a sectional view of a focusing ultrasonic transducer element according to a fourth embodiment of the present invention. The same reference numerals as used in FIG. 7 denote the same parts in FIG. 11. In this embodiment, an acoustic impedance matching layer 34 is attached on the concave cylindrical portion 24 of the ultrasonic propagating medium 22 in the same way as the embodiment in FIG. 10 and this function and effect are the same as those of the embodiment in FIG. 10.

What is claimed is:

1. A focusing ultrasonic transducer element comprising an ultrasonic propagating medium having a convex spherical portion with a convex spherical surface in one end thereof and a concave spherical portion with a concave spherical surface in the other end thereof and an ultrasonic transmitting and receiving transducer attached on the surface of said convex spherical portion, an axis of symmetry of said convex spherical portion being aligned with that of said concave spherical portion and a center point of said convex spherical portion being offset from that of said concave spherical portion.

2. A focusing ultrasonic transducer element according to claim 1, wherein said ultrasonic propagating medium is comprised of sapphire.

3. A focusing ultrasonic transducer element according to claim 1, wherein said ultrasonic propagating medium is comprised of fused quartz.

4. A focusing ultrasonic transducer element according to claim 1, wherein an acoustic impedance matching layer is attached on said concave spherical portion.

5. A focusing ultrasonic transducer element comprising an ultrasonic propagating medium having a convex cylindrical portion with a convex cylindrical surface in one end thereof and a concave cylindrical portion having a concave cylindrical surface in the other end thereof and an ultrasonic transmitting and receiving transducer attached on the surface of said convex cylindrical portion, an axis of symmetry of said convex cylindrical portion being aligned with that of said concave cylindrical portion and a center point of said convex cylindrical portion being offset from that of said concave cylindrical portion.

6. A focusing ultrasonic transducer element according to claim 5, wherein said ultrasonic propagating medium is comprised of sapphire.

7. A focusing ultrasonic transducer element according to claim 5, wherein said ultrasonic propagating medium is comprised of fused quartz.

8. A focusing ultrasonic transducer element according to claim 5, wherein an acoustic impedance matching layer is attached on said concave cylindrical portion.

* * * * *